United States Patent [19]

Trailer

[11] Patent Number: 5,154,387
[45] Date of Patent: Oct. 13, 1992

[54] METHOD AND APPARATUS FOR ESOPHAGEAL PACING

[75] Inventor: Dennis R. Trailer, Cape Coral, Fla.

[73] Assignee: Syncromed Corporation, Tampa, Fla.

[21] Appl. No.: 531,418

[22] Filed: May 31, 1990

[51] Int. Cl.$^5$ .............................................. A61N 1/05
[52] U.S. Cl. .................................... 128/784; 128/786; 128/642; 128/419 P
[58] Field of Search ................... 128/419 P, 786, 642, 128/784

[56] References Cited

U.S. PATENT DOCUMENTS

| | | | |
|---|---|---|---|
| 3,951,136 | 4/1976 | Wall | 128/642 |
| 4,176,660 | 12/1979 | Mylrea et al. | 128/671 |
| 4,349,031 | 9/1982 | Perlin | 128/642 |
| 4,475,555 | 10/1984 | Linder | 128/670 |
| 4,476,872 | 10/1984 | Perlin | 128/642 |
| 4,574,807 | 3/1986 | Hewson et al. | 128/786 |
| 4,603,705 | 8/1986 | Speicher et al. | 128/419 D |
| 4,619,268 | 10/1986 | Uphold and Phohl | 128/671 |
| 4,693,258 | 9/1987 | Osypka et al. | 128/783 |
| 4,763,663 | 8/1988 | Uphold and Phohl | 128/671 |
| 4,817,611 | 4/1989 | Arzbaecher et al. | 128/642 |
| 4,848,352 | 7/1989 | Pohndorf et al. | 128/642 |
| 4,930,521 | 6/1990 | Metzger et al. | 128/786 |
| 5,069,215 | 12/1991 | Jadver et al. | 128/642 |
| 5,109,851 | 5/1992 | Jadver et al. | 128/642 |

OTHER PUBLICATIONS

"Lead Configurations in Esophageal Electrocardiography," H. Jadvar et al., 21 Medical Instrumentation 158 (Jun. 1987).
"Transesophageal Atrial Pacing", B. Phillips et al., Medical Electronics (Dec. 1987).
"The Arzco Tapsul® Pill Electrode and Preamplifier," Arzco Medical Electronics, Inc. (undated).
"The Stat-Pace II Transesophageal Cardiac pacer," Seecor, Inc. (undated).

Primary Examiner—William E. Kamm
Assistant Examiner—Scott M. Getzow
Attorney, Agent, or Firm—Lowe, Price, LeBlanc & Becker

[57] ABSTRACT

The method and apparatus for emergency pacing of a surgical patient's heart through an esophageal catheter. Pacing electrodes are connected to the external wall of the catheter having sufficient surface area to reduce the current density to a level which does not burn or injure the patient's esophagus. Pacing pulses are applied to the electrodes by a pacing generator and the pulses are transmitted through the esophagus wall to the patient's heart.

13 Claims, 2 Drawing Sheets

5,154,387

METHOD AND APPARATUS FOR ESOPHAGEAL PACING

TECHNICAL FIELD

This invention relates generally to an apparatus for and method of emergency pacing of a surgical patient's heart and more particularly to an apparatus for and method of emergency pacing during surgery through an esophageal catheter.

BACKGROUND OF THE INVENTION

It is common practice during surgical procedures in which the patient is subjected to a general anesthetic to monitor various body functions using a flexible catheter inserted through the patients' nose into the esophagus. For example, U.S. Pat. Nos. 4,476,872, 4,439,031, 4,176,660 and 3,951,136 disclose an esophageal catheter used for monitoring the patient's electrocardiogram, heartbeat and temperature. Similarly, U.S. Pat. Nos. 4,763,663 and 4,619,268 disclose esophageal catheters which monitor heart sounds and body temperature. U.S. Pat. No. 4,475,555 discloses an esophageal probe with a universal measuring attachment to which may be adapted a stethoscope for measuring body sounds, a temperature sensor for measuring body temperature, pressure transducers or light sources.

Two prior art esophageal catheters include electrodes which may be used for diagnostic pacing. One such device is the Azbacher Pill Electrode for diagnostic pacing; the second is the Seecor Model Stat Pace II transvenous wire which may be fed into the esophagus. In these devices the patient's heart is temporarily paced to a high rate, such as 120 beats per minute, the pacing signal is removed and the patient's heart is then monitored with the ECG sensor to determine the rate and function to which it returns after removal of the diagnostic pacing pulses. The pacing electrodes in these catheters, however, have a relatively small surface area and thus generate a high current density which would burn the patient's esophagus if pacing continued beyond a short period of time.

A problem present in every surgical procedure in which the patient is administered a general anesthesia is the possibility that the patient's heart will beat erratically or too slowly or cease functioning completely in response to the anesthesia or stresses of surgery. In such cases the anesthesiologist and other members of the surgical team must act quickly to restore the patient's heart to its normal rhythm. This is typically done by applying an external pacer to the patient. Doing so, however, requires that at least one external electrode be applied to the patient's chest. In some surgical procedures it is difficult, if not impossible, to employ these emergency procedures. For example, if the patient is undergoing back surgery, he may be positioned face down on the operating table and incapable of movement without severe injury, so that application of the pacing electrodes may be extremely hazardous to the patient.

SUMMARY OF THE INVENTION

Accordingly, one object of the invention is to provide an emergency pacemaker which may be quickly and easily utilized during surgical procedures performed under general anesthesia.

Another object of the invention is to provide an emergency pacemaker which is incorporated with an esophageal catheter used during surgical procedures performed under general anesthesia.

Yet another object of the invention is to provide an esophageal catheter which may be used for emergency pacing of the patient's heart during surgical procedures.

Still another object of the invention is to provide a method for readily pacing a patient's heart during surgical procedures during which the patient is administered general anesthesia.

Another object of the invention is to provide pacing electrodes which may be used with an esophageal catheter for emergency pacing of a patient's heart and which do not cause injury to the patent's esophagus during pacing.

Yet another object of the invention is to provide a method for readily pacing a patient's heart in an emergency situation in the Intensive Care Unit, Coronary Care Unit, or any other area of the hospital that a patient may develop arrhythmias or experience cardiac arrest.

These and other objects are achieved by an emergency pacemaker for continuously pacing the heartbeat of a patient comprising a flexible catheter for insertion into the patient's esophagus, a pair of spaced pacing electrodes along the external wall of the catheter, a pacing generator which generates an electrical signal used to pace the patient's heart, and a pair of electrical conductors located in the interior portion of the catheter connecting the pacing electrodes to the pacing generator.

In accordance with another aspect of the invention, the foregoing and other objects are achieved by providing an esophageal catheter for use during surgery which includes pacing electrodes connected to the external wall of the esophageal catheter for pacing the patient's heart directly through the esophagus wall. The electrodes are of sufficient surface area to reduce the current density to a level which does not burn or otherwise injure the patient's esophagus.

In accordance with another aspect of the invention, the foregoing and other objects are obtained by providing a method for continuously pacing a patient's heart during surgery in which the patient has been administered a general anesthetic by inserting a flexible catheter into the patient's esophagus which includes a pair of spaced pacing electrodes that are electrically coupled to a pacing generator. Pacing pulses are then applied to these electrodes by the generator and these electrodes transmit the pulses through the esophagus wall to the patient's heart.

Still other objects and advantages of the present invention will become readily apparent to those skilled in this art from the following detailed description, wherein only the preferred embodiment of the invention is shown and described, simply by way of illustration of the best mode contemplated for carrying out the invention. As will be realized, the invention is capable of other and different embodiments, and its several details are capable of modifications in various and obvious respects, all without departing from the invention. Accordingly, the drawings and description are to be regarded as illustrative in nature and not as restrictive.

DESCRIPTION OF THE PREFERRED EMBODIMENT

Esophageal catheters are commonly used for surgical procedures for which a general anesthetic is administered to the patient. After the anesthesia has been administered and the patient becomes unconscious, a flexible plastic catheter is inserted through the patient's nose and down his esophagus until the distal end of the catheter strikes the bottom of the esophagus.

Figure 1:
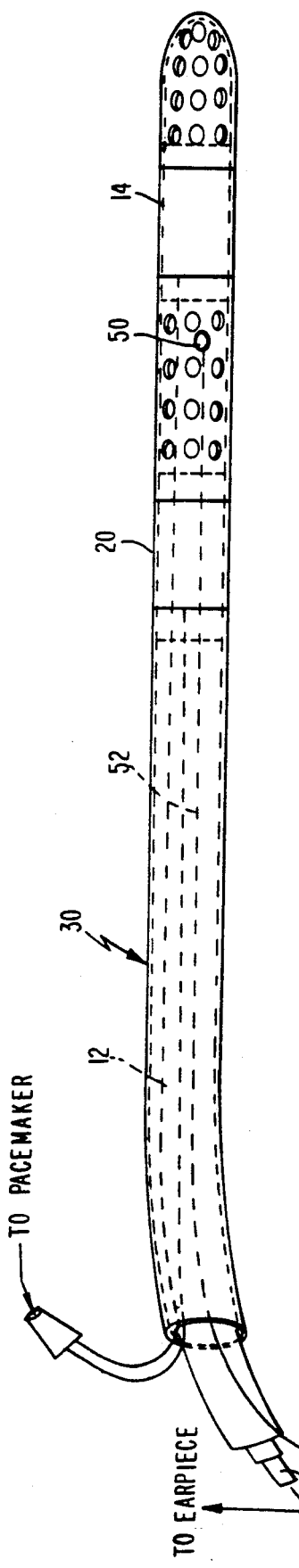
FIG. 1 is a diagram of the esophageal catheter of the present invention.

Referring to FIG. 1, the esophageal catheter 30 of the present invention comprises a flexible plastic tube which is typically about 35 centimeters in length, an example of which is the Monotherm. The interior portion of the tube is hollow for flexibility and also to allow implementation of various medical devices, as discussed hereinafter. Distal pacing electrode 14 and proximal pacing electrode 20 are positioned along catheter 30, with distal pacing electrode 14 closer to the distal end of catheter 30 and proximal pacing electrode 20 spaced therefrom and positioned closer to the proximal end of catheter 20.

The portion of catheter 30 lying between the pacing electrodes and the portion of catheter 30 to the distal side of electrode 14 together form a stethoscope, as described in greater detail hereinafter, for monitoring the patient's body sounds. The proximal end of catheter 30 has a fitting 42 which can be connected to a conventional ear piece (not shown) for listening to these sounds. A conventional thermistor 50, such as the Monotherm, is positioned between electrodes 14 and 20. Thermistor 50 is connected to wire 52, which is threaded through catheter 30 and connected at its proximal end to a conventional connector 54. This connector is inserted into a conventional temperature monitor, not shown, for monitoring the patient's temperature during surgery.

Figure 2:
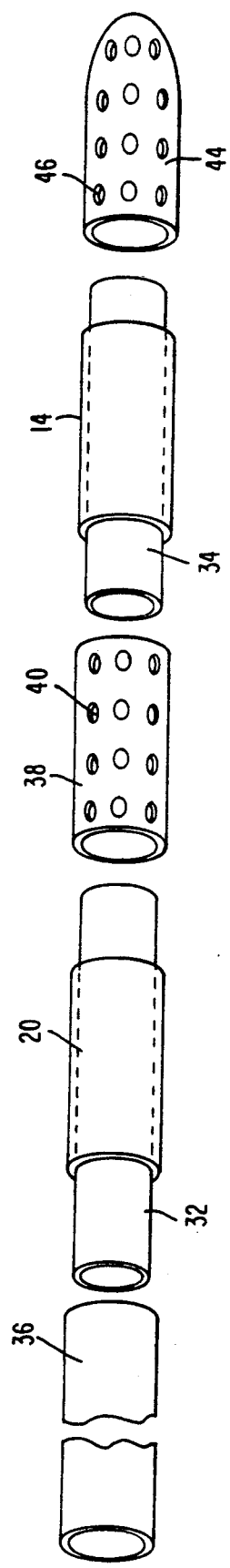
FIG. 2 is an exploded view of the pacing electrodes and distal end of the esophageal catheter of the present invention.

Reference is now made to FIG. 2, which is an exploded view of the pacing electrode assembly. A flexible tube 32 having an outside diameter slightly less than the inside diameter of proximal pacing electrode 20 is inserted into the hollow portion of electrode 20. Electrode 20 is secured to tube 32 by suitable means, such as medical grade adhesive or by crimping. Similarly, flexible tube 34 having an outside diameter slightly less than the inside diameter of distal pacing electrode 14 is inserted into the hollow portion of electrode 14 and secured to it in the same fashion.

Tube 32 is then inserted into tube 36, the other end of which terminates at the proximal end of pacing catheter 30. The outer diameter of tube 32 is slightly smaller than the inner diameter of tube 36 and the two are secured together with cement. The distal end of tube 32 is inserted into an intermediate tube 38 having approximately the same outer diameter as tube 36. In the preferred embodiment tube 38 has a series of openings 40 spaced around the periphery, forming a stethoscope, as described above. To prevent fluids from entering the interior of catheter 30, a thin, flexible membrane (not shown) is fitted over tube 38. The proximal end of tube 34 is inserted into the distal end of tube 38 and cemented thereto for a secure fit in the manner described above.

The distal end of catheter 30 comprises a flexible tube 44 having the same outer diameter as tubes 36 and 38 and an inner diameter which is slightly larger than the outer diameter of tube 34. The distal end of tube 44 is sealed off and the proximal end is fitted over and cemented to the distal end of tube 34, as above. Tubular portion 44, like tube 38, has holes 46 spaced around the periphery which form a stethoscope for acoustically coupling body sounds to ear piece 42. Tubular portion 44 also has a thin flexible membrane on its outer surface (not shown) to prevent liquids from entering the interior portion of catheter 30.

In the preferred embodiment the outer diameter of pacing electrodes 14 and 20 are equal to the outer diameter of tubes 36, 38 and 46, so that the catheter, when assembled, presents essentially a smooth continuous surface, thereby enabling easy insertion into and removal from the patient's esophagus.

It should be understood that operation of the stethoscope is independent from operation of the pacemaker and, therefore, that inclusion of the stethoscope is optional. For example, in an alternative embodiment tubes 38 and 46 would be unperforated and identical to tube 36. Similarly, inclusion of thermistor 50 is also optional.

Figure 3:
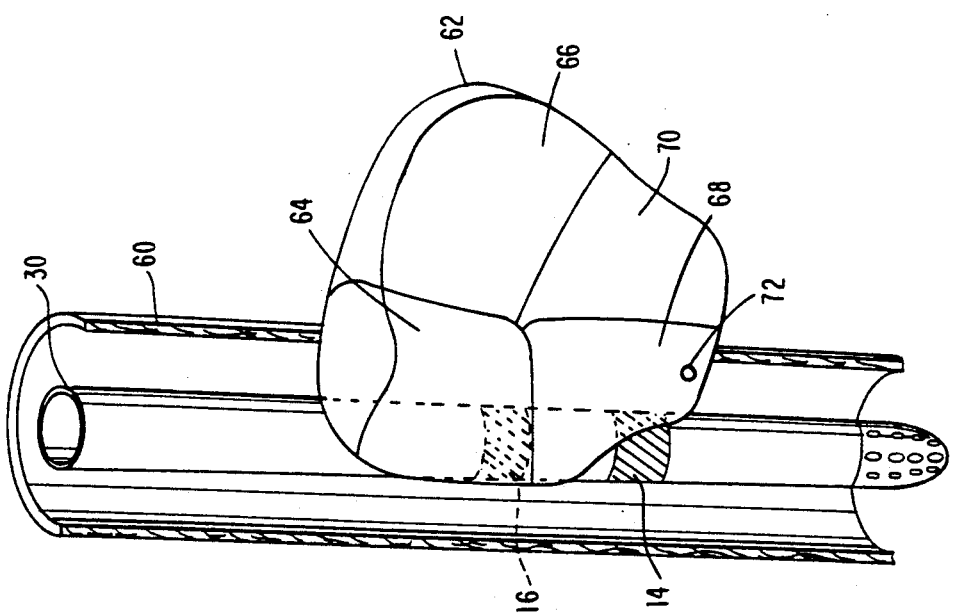
FIG. 3 is a perspective view of the esophageal catheter of the present invention inserted into the patient's esophagus.

The positioning of esophageal catheter 30 relative to the patient's esophagus and heart is shown in FIG. 3. Catheter 30 is fed through the patient's nose into his esophagus 60. Esophagus 60 lies behind and slightly to the left of heart 62. Heart 62 comprises four chambers, a right atrium 64, left atrium 66, right ventricle 68 and left ventricle 70. Right ventricle 68 has a sinus node 72 which responds to electrical pacing signals, causing the heart chambers to contact and pump blood. As is well known in the art, pacing may occur by applying pacing pulses to the right ventricle or right atrium which cause these chambers to constrict, respectively. Primary pumping action occurs, however, by contraction of the right ventricle. Pacing electrodes 14 and 16 are positioned on catheter 30 so that the pacing pulses cause both the right ventricle and right atrium to constrict, thereby maximizing pacing efficiency.

Pacing electrodes 14 and 20 must allow sufficient current flow to cause ventricular and atrial pacing and must be large enough to prevent excessive current densities which can injure the esophagus. It has been found by the inventors that the pacing electrodes should have a minimum surface area of approximately 1.5 square centimeters to achieve these results. For a standard size catheter of 2.5 millimeters diameter, this means that the pacing electrodes should be approximately 2.0 centimeters long to achieve these results. Since the pacing electrodes are inserted into the esophagus with pacing catheter 30, they are made of a conducting metal which does not react with body fluids, such as platinum and stainless steel.

Figure 4:
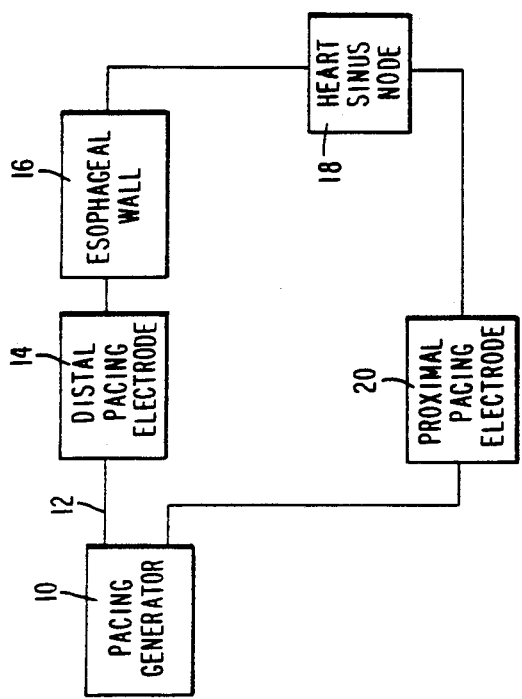
FIG. 4 is a block diagram of the emergency pacing apparatus of the present invention.

Operation of the emergency pacing apparatus of the present invention is shown with reference to FIG. 4. A conventional pacing generator 10, such as the Seecor Stat Pace II or Synchromed's EP 1000, generates pacing pulses which are output on line 12 to distal pacing electrode 14 in esophageal catheter 30. The pacing pulse is transmitted from electrode 14 through the patient's esophageal wall 16 to the patient's right ventricle and right atrium, thereby causing the heart to beat in response to these pulses. The electrical return or ground path for the pacing pulse is through proximal pacing electrode 20 back to pacing generator 10.

The stimulus or pacing current is controlled via a pulse generator. The pulse generator has a variable voltage, constant current power supply. A digital display indicates the current in milliamperes delivered to the heart via the esophageal pacing electrodes. A conventional current controller increases or decreases the current delivered to the patient. The pulse generator has a range of 1.5 milliamperes (mA) to 25 mA.

While there has been described and illustrated one specific embodiment of the invention, it will be clear that variations in the details of the embodiments specifically illustrated and described may be made without departing from the true spirit and scope of the invention as defined in the appended claims.

What is claimed is:

1. An emergency pacemaker for continuously pacing the heart of a patient comprising:
    a flexible catheter for insertion into the esophagus of said patient, said catheter having a proximal end, a distal end and an exterior wall;
    first and second pacing electrodes coupled to said catheter, said first pacing electrode being closer to the distal end of said catheter than said second pacing electrode;
    a pacing generator for generating electrical pulses used to pace the patient's heart, wherein each of said electrodes is of sufficient surface area to prevent injuring said patient's esophagus during continuous emergency pacing; and
    a pair of electrical conductors located in the interior portion of said catheter, one of which is connected between said first pacing electrode and said pacing generator for conducting said pulses to said first pacing electrode and the other of which is connected between said second pacing electrode and said pacing generator for conducting said electrical energy between said second pacing electrode and said pacing generator.

2. The emergency pacemaker of claim 1, wherein each of said pacing electrodes is a hollow metal cylinder which is coupled to the exterior wall of said catheter.

3. The emergency pacemaker of claim 2, wherein each of said pacing electrodes has a length along its longitudinal axis exceeding 2.0 centimeters.

4. The emergency pacemaker of claim 1, wherein each of said pacing electrodes conducts electrical current at a current density of less than 25 milliamperes per square centimeter.

5. The emergency pacemaker of claim 1, wherein each of said pacing electrodes has a surface area of at least 1.5 square centimeters.

6. A catheter used with a surgical patient and having a distal end and a proximal end, comprising:
    a hollow elongated flexible tube for insertion into the esophagus of said patient; and
    a pair of spaced electrodes coupled to said tube for continuously transmitting electrical energy through the wall of said esophagus to said patient's heart for pacing said heart, wherein each of said electrodes is of sufficient surface area to prevent injuring said patient's esophagus during continuous emergency pacing.

7. The catheter of claim 6, wherein said electrodes transmit said energy at a current density of less than 25 milliamperes per square centimeter.

8. The catheter of claim 6, further comprising means positioned in the interior of said flexible tube for monitoring the patient's internal body temperature.

9. The catheter of claim 6, further comprising means for transmitting sounds generated by the patient's heart from said distal end of said catheter to said proximal end of said catheter.

10. The catheter of claim 6, wherein each of said electrodes has a surface area of at least 1.5 square centimeters.

11. The catheter of claim 6, wherein each of said electrodes comprises a cylindrical hollow body having a length along its longitudinal axis exceeding 2.0 centimeters.

12. A method of continuously pacing a patient's heart during surgery comprising:
    inserting a flexible catheter into the esophagus of said patient, said catheter including a pair of spaced electrodes electrically coupled to a pacing generator;
    generating pacing pulses in said pacing generator;
    transmitting said pacing pulses from said generator to one of said electrodes; and
    transmitting said pacing pulses from said electrode through the wall of said esophagus to the patient's heart, wherein each of said electrodes is of sufficient surface area to prevent injuring said patient's esophagus during continuous emergency pacing.

13. The method of claim 12, wherein the current density of said pacing pulses transmitted from said electrodes is less than 25 milliamperes per square centimeter.

* * * * *